United States Patent
Okada

(10) Patent No.: US 6,881,225 B2
(45) Date of Patent: Apr. 19, 2005

(54) INTRAOCULAR LENSES WITH A GROOVE FOR CLOSING THE OPENING OF THE POSTERIOR CAPSULE

(76) Inventor: Kiyoshi Okada, 3-8-23, Higashi Tsutsujigaoka, Chofu-shi, Tokyo (JP), 182-0005

( * ) Notice: Subject to any disclaimer, the term of this patent is extended or adjusted under 35 U.S.C. 154(b) by 0 days.

(21) Appl. No.: 10/317,840

(22) Filed: Dec. 10, 2002

(65) Prior Publication Data

US 2003/0187501 A1 Oct. 2, 2003

Related U.S. Application Data

(63) Continuation of application No. 09/627,483, filed on Jul. 28, 2000, now abandoned.

(51) Int. Cl.$^7$ .................................................. A61F 2/16
(52) U.S. Cl. ..................... 623/6.4; 623/6.43; 623/6.44; 623/6.54
(58) Field of Search .............................. 623/6.44, 6.54, 623/6.11, 6.12, 6.34, 6.37–6.4, 6.43, 6.47, 6.49

(56) References Cited

U.S. PATENT DOCUMENTS

| 5,171,320 | A | | 12/1992 | Nishi |
| 5,476,512 | A | * | 12/1995 | Sarfarazi .................... 623/6.39 |
| 5,697,973 | A | | 12/1997 | Peyman et al. |
| 6,027,531 | A | | 2/2000 | Tassignon |

FOREIGN PATENT DOCUMENTS

| EP | 0 916 320 A2 | * | 5/1999 | ............. A61F/2/16 |
| WO | WO 99/62435 | | 12/1999 | |

* cited by examiner

Primary Examiner—David H. Willse
(74) Attorney, Agent, or Firm—Knobbe Martens Olson & Bear LLP

(57) ABSTRACT

An intraocular lens structure for reducing complications is disclosed. The intraocular lens structure comprises an optic, a support and a closing fixture. The closing fixture is a groove or a valley formed on the side portion of the optic of the intraocular lens. The valley is formed by the optic and a protrusion projecting posteriorly from the optic. The groove or the valley in the optic is made engaged with the posterior capsular opening generally over the entire circumference of the groove or the valley to close the opening of the posterior capsule.

14 Claims, 5 Drawing Sheets

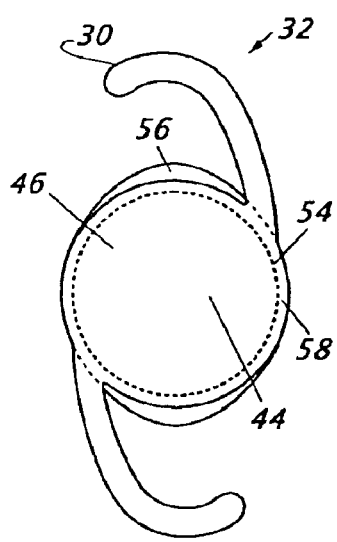 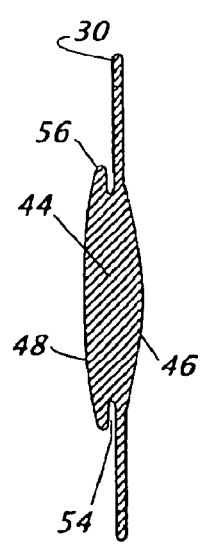 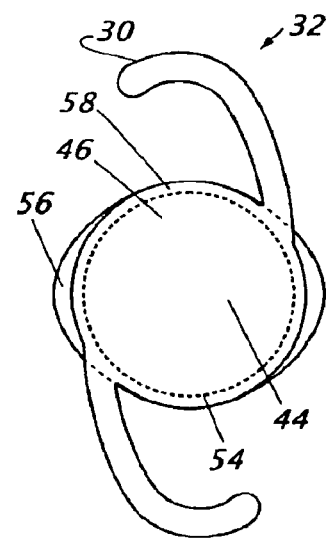
*Fig. 7a*  *Fig. 7b*  *Fig. 8*
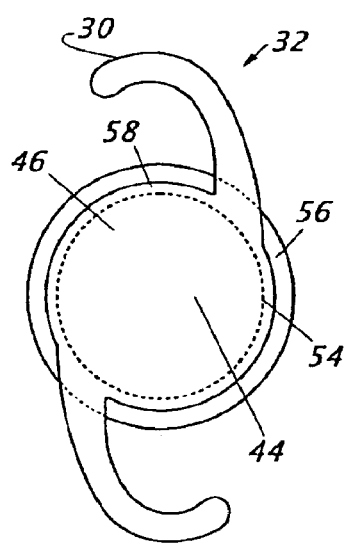 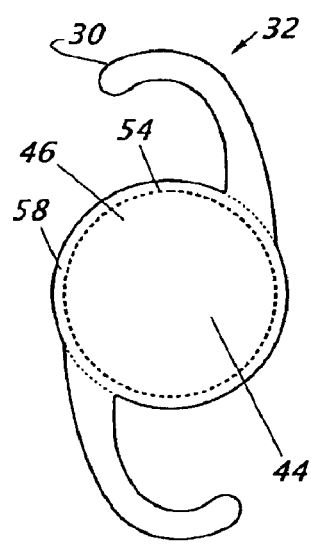
*Fig. 9*  *Fig. 10*

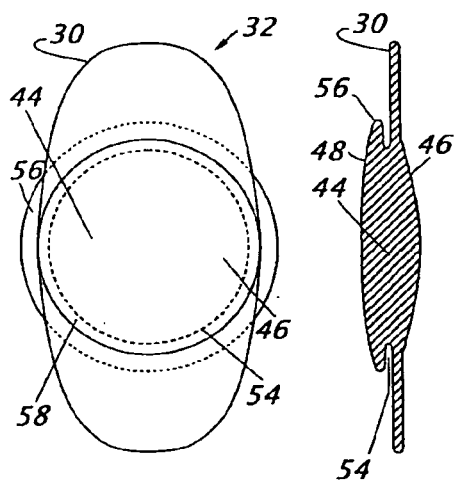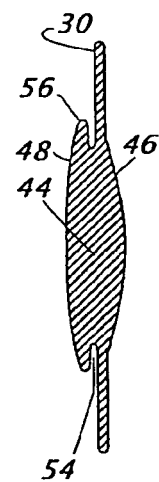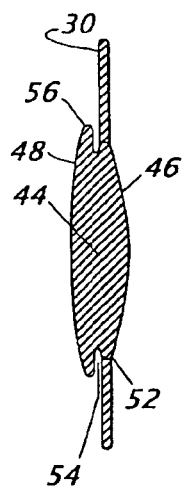
Fig. 11a    Fig. 11b    Fig. 11c    Fig. 11d
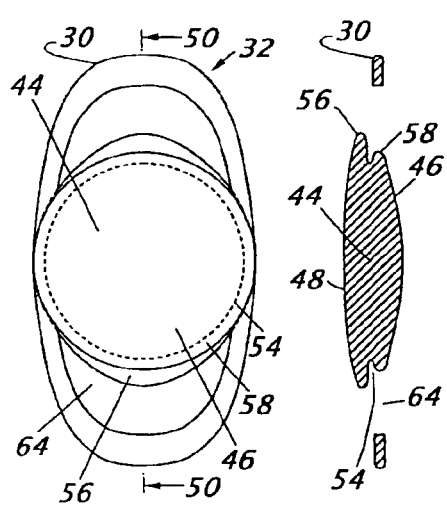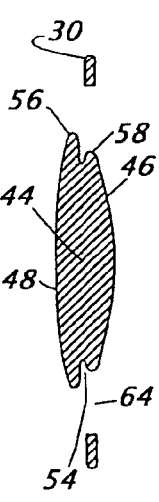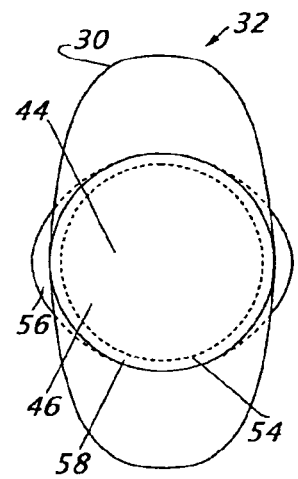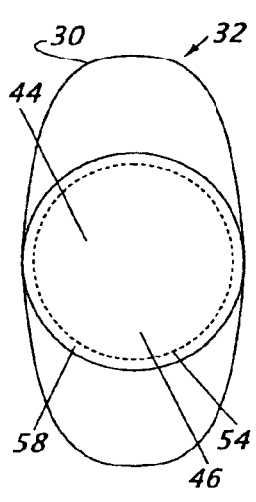
Fig. 12a    Fig. 12b    Fig. 13    Fig. 14

INTRAOCULAR LENSES WITH A GROOVE FOR CLOSING THE OPENING OF THE POSTERIOR CAPSULE

RELATED APPLICATIONS

This application is a continuation of U.S. application Ser. No. 09/627,483, filed Jul. 28, 2000, now abandoned.

FIELD OF THE INVENTION

The present invention relates generally to cataract surgery, particularly to intraocular lenses and the use thereof for reduction in complications related to the surgery.

BACKGROUND OF THE INVENTION

When an eye develops a cataract and the natural lens becomes clouded, the lens materials, i.e., lens cortex and lens nucleus, are removed through an opening made in the anterior capsule. It is called extracapsular cataract extraction. In most of the cases, intraocular lenses are implanted in the residual lens capsule called the lens capsular bag. It is difficult to remove lens epithelial cells during cataract surgery. Postoperatively lens epithelial cells proliferate and migrate toward the center part of the residual posterior capsule to cause visual disturbance. This process is called posterior capsular opacification or secondary cataract. The clouded posterior capsule with proliferated lens epithelial cells can be disrupted by YAG laser and the visual axis can be cleared to restore the vision. This treatment is called YAG laser capsulotomy. However, the YAG laser treatment exposes patients to the risk of severe visual impairment or loss of vision by developing retinal detachment, cystoid macula edema and glaucoma. The development of retinal detachment and cystoid macular edema following the YAG laser treatment is thought to be related to the disruption of the anatomical barrier of the posterior capsule and the loss of the stability of the vitreous. In addition, the instrument required for YAG laser capsulotomy is expensive as is the cost for the treatment. Accordingly, there is a great need for a method to reduce the complications related to cataract surgery.

There have been many attempts to eliminate posterior capsular opacification. One promising attempt is to remove central areas of the anterior and the posterior lens capsules in a circular fashion, and fix an intraocular lens by the anterior and the posterior lens capsules (U.S. Pat. No. 6,027,531 to Tassignon.). However, there are some drawbacks of the intraocular lens and the use thereof. One of the drawbacks of the intraocular lens is a lack of stability, especially in early postoperative days. This is because, during the one week following cataract surgery, the posterior capsule is not taut. There is a risk of luxation of the intraocular lens into the anterior chamber or into the vitreous. In addition, the visual acuity will not be stable while the lens capsule is not taut in the early postoperative days. Furthermore, it is technically difficult to adjust and fix the intraocular lens to the openings of both the anterior and the posterior lens capsules.

From a different point of view, an intraocular lens for fixation by a lens capsular opening was disclosed by U.S. Pat. No. 5,697,973. The disclosed intraocular lens is intended for use when the capsular bag is destroyed during removal of a cataract. The intraocular lens comprises a lens and an annular ring having upper flange and lower flange and an inner wall interconnecting said flanges. Alternatively, an intraocular lens disclosed in U.S. Pat. No. 5,697,973 has a plurality of concentric circular grooves. The structures of the disclosed intraocular lenses are very complicated for manufacturing.

SUMMARY OF THE INVENTION

The present invention provides intraocular lenses and the use thereof for reducing complications related to cataract surgery. Due to the use of the intraocular lenses of the present invention, complications related to cataract surgery such as retinal detachment and cystoid macula edema are substantially eliminated or reduced. This is achieved by implantation of an intraocular lens comprising: an optic; a support, wherein said support extends outwardly from the optic anterior to a groove or a valley, wherein said groove is formed in the side portion of the optic of the intraocular lens, wherein said valley is formed by the optic and a protrusion, wherein said protrusion projects posterior from the posterior surface of the optic of the intraocular lens, wherein said support supports the optic; and a closing fixture for the opening of the posterior capsule, wherein the closing fixture is the groove or the valley, wherein the groove or the valley is made engaged with the posterior capsular opening generally over the entire circumference of the groove or the valley, whereby said posterior capsular opening is closed.

A further embodiment of the present invention is to provide intraocular lenses for closing an opening of the posterior capsule. An intraocular lens in accordance with the present invention has a closing fixture, wherein said closing fixture is a groove or a valley, wherein said groove is formed in the side portion of the optic, wherein said valley is formed by the optic and a protrusion extending posterior from the posterior surface of the optic of the intraocular lens. The groove or the valley of the intraocular lens engages with the opening of the posterior capsule generally over the circumference to close the opening, whereby the stability of the vitreous is maintained to minimize the possibility to develop retinal detachment and cystoid macula edema following cataract surgery.

A further embodiment of the present invention is to provide an intraocular lens having an optic with a closing fixture for closing the opening of the posterior capsule. Since the closing fixture is formed in the optic, the intraocular lens has a relatively simple structure for manufacturing without difficulty. It reduces the cost for manufacturing the intraocular lens.

A further embodiment of the present invention is to provide a method to complete cataract surgery using intraocular lenses provided by the present invention. According to the present invention, the method for closing the opening of the posterior capsule comprising: making an incision in the anterior part of the eye, making an opening in the anterior capsule, making an opening in the posterior capsule, placing an intraocular lens in the lens capsular bag, and closing the opening of the posterior capsule by the groove or the valley of the intraocular lens, wherein said intraocular lens is provided in accordance with the present invention.

Accordingly, the present invention provides an intraocular lenses and the use thereof for reducing complications related to cataract surgery. It will also eliminate the costs related to YAG laser capsulotomy.

BRIEF DESCRIPTION OF THE DRAWINGS

FIG. 7a is a plan view of a sixth embodied intraocular lens illustrating one piece intraocular lens with posterior portions extending in the direction of the long axis of the lens.

FIG. 7b is a side view of the intraocular lens shown in FIG. 7a, illustrating a biconvex optic.

FIG. 8 is a plan view of a seventh embodied intraocular lens with posterior portions forming an oval configuration in the direction perpendicular to the long axis of the lens.

FIG. 9 is a plan view of an eighth embodied intraocular lens having posterior portion extending in a circular fashion.

FIG. 10 is a plan view of a ninth embodied intraocular lens of one-piece intraocular lens.

FIG. 11a is a plan view of a tenth embodied intraocular lens with plate haptics of an oval shape illustrating posterior portion extending in a circular fashion.

FIG. 11b is a side sectional view of the intraocular lens shown in FIG. 11a of a one-piece biconvex optic.

FIG. 11c is a side sectional view of the intraocular lens shown in FIG. 11a of a biconvex optic attached.

FIG. 11d is a side sectional view of the optic of the intraocular lens shown in FIG. 11a.

FIG. 12a is a plan view of an eleventh embodied intraocular lens having plate haptics. Each haptic has a window.

FIG. 12b is a cross sectional view of the intraocular lens of FIG. 12a taken along line 50—50 of FIG. 12a.

FIG. 13 is a plan view of a twelfth embodied intraocular lens having plate haptics of an oval shape. The intraocular lens has posterior portions extending in an oval fashion.

FIG. 14 is a plan view of a thirteenth embodied intraocular lens with plate haptics of an oval shape.

REFERENCE NUMERICALS IN DRAWINGS

Figure 1:
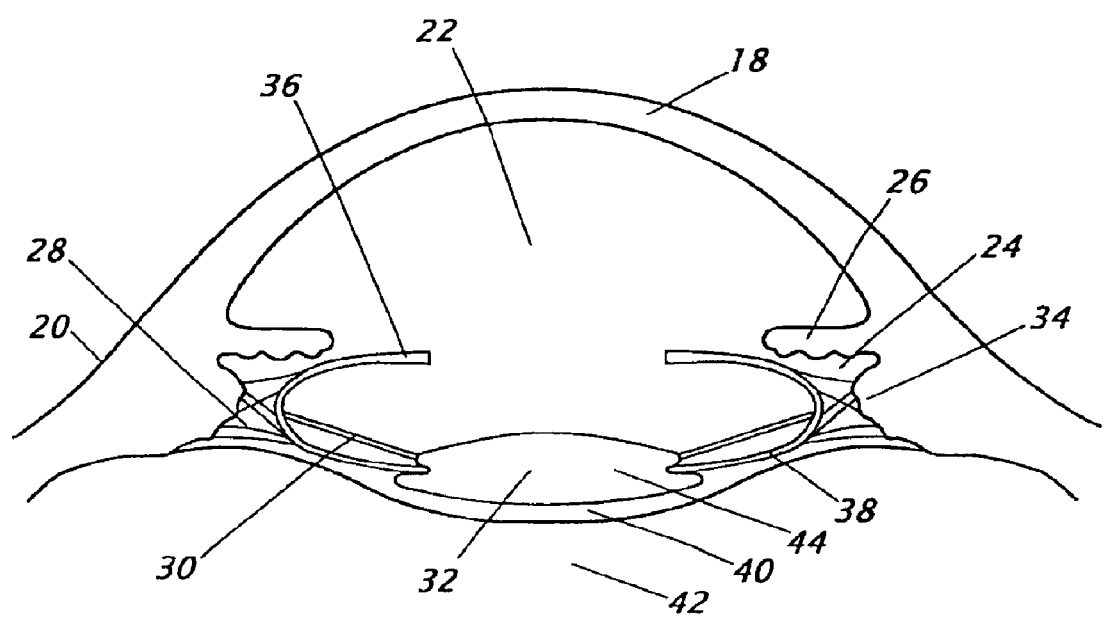
FIG. 1 is a sectional view of a human eye that has received an intraocular lens implantation in accordance with the present invention.

18: Cornea
20: Sclera
22: Anterior chamber
24: Posterior chamber
26: Iris
28: Zonules
30: Haptic
32: Intraocular lens
34: Ciliary body
36: Anterior capsule
38: Posterior capsule
40: Berger's space
42: Vitreous
44: Optic
46: Anterior surface of the optic
48: Posterior surface of the optic
50: Line indicating a cross section for FIG. 12b
52: Connection between the optic and a haptic
54: Groove
56: Posterior portion
58: Anterior portion
60: Protrusion of the optic
62: Valley
64: Window in the haptic
66: Height of the posterior portion
68: Depth of the groove

DESCRIPTION OF THE PREFERRED EMBODIMENTS

The present invention provides intraocular lenses and the use thereof for reducing complications related to cataract surgery. By using the intraocular lenses, the related complications such as cystoid macular edema, retinal detachment and posterior capsular opacification are substantially eliminated or reduced. This is achieved by making a substantially circular opening in the posterior capsule and implanting the intraocular lens of the present invention in the lens capsular bag to close the opening of the posterior capsule.

In accordance with the present invention, any intraocular lens, comprising the optic, support and closing fixture for the opening of the posterior capsule, may be used, wherein said support extends outwardly from the optic anterior to the groove in the side portion of the optic, whereby said support supports the optic in the lens capsular bag, wherein the closing fixture is a groove or a valley, wherein said groove is in the side portion of the peripheral part of the optic, wherein said valley is formed by the optic and a protrusion extending posterior from the posterior surface of the optic of the intraocular lens. Alternatively, the closing fixture which closes the opening of the posterior capsule may be included in the optic. The opening of the posterior capsule engages with the groove or the valley generally over the entire circumference to close the posterior capsular opening. By closing the opening of the posterior capsule, the anatomical barrier is restored so that the stability of the vitreous is maintained and the development of cystoid macular edema and retinal detachment following cataract surgery is minimized. Also, due to the removal of the center part of the posterior capsule and the closing of the opening of the capsule, migration and proliferation of lens epithelial cells toward the visual axis following cataract surgery is blocked at the groove or the valley. This eliminates the visual disturbance due to the proliferation and migration of lens epithelial cells toward the visual axis on the posterior capsule. An intraocular lens in accordance with the present invention may have a support for a haptic or haptics of any configuration and may have an optic made of any material acceptable for clinical use. The material for the optic of an intraocular lens to be used includes, but is not limited to, silicone, hydrogel, acrylic polymer and a combination of two or more of this group. The term "acrylic polymer" includes polyalkylacrylates, such as polymethylmethacrylate, as well as copolymers of two or more acrylic monomers such as methylmethacrylate and buthylmethacrylate. A groove is formed in the side portion of the optic in a substantially annular fashion generally perpendicular to an optical axis of the lens. The optic of intraocular lenses may be biconvex, convex-plano (plano posterior), plano-convex, or concave for at least one optic surface. Indeed, the optic of the intraocular lenses in accordance with the present invention may be a multifocal, toric or telescopic lens for the specific purposes.

FIG. 1 depicts a side sectional view of an eye in which an intraocular lens 32 is implanted according to the present invention. This figure illustrates the anatomy of the eye related to cataract surgery. That is, the anterior part of the eye comprises a cornea 18, sclera 20, iris 26, anterior chamber 22, ciliary body 34 and zonules 28. The posterior chamber 24 is the space behind the iris 26 and anterior to the vitreous 42. For implantation of an intraocular lens 32, anterior capsulotomy is performed and an opening is made in the anterior capsule 36. The clouded lens is removed to leave the lens capsular bag. The center region of the posterior capsule 38 is removed, preferably, in a circular fashion. The intraocular lens 32 is engaged with the opening of the posterior capsule 38 to close the opening of the posterior capsule 38. A haptic or haptics 30 in the lens capsular bag support or supports the optic 44 of the intraocular lens 32. Vitreous 42 is located posterior to the posterior capsule 38. The space between the anterior face of the vitreous 42 and the posterior capsule 38 is called Berger's space 40.

Examples of preferred embodiments of the present inventions are illustrated in FIGS. 1–14. As will readily be appreciated by those skilled in the art, the following specific embodiments are merely illustrative of the wide variety of intraocular lenses included within the spirit and scope of the present invention.

Figure 2A:
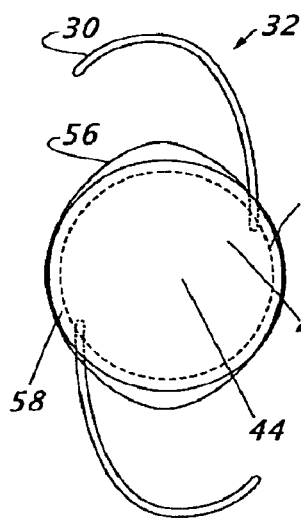
FIG. 2a is a plan view of one embodied form of an intraocular lens having posterior portions of the optic extending in an oval fashion in the direction of the long axis of the lens.

FIG. 2a depicts a plan view of an intraocular lens 32 in accordance with the present invention. The intraocular lens 32 has a substantially circular optic 44 for projecting images on the retina and two haptics 30 to support the optic 44 of the intraocular lens 32. The two haptics 30 extend from the optic 44 outwardly. The haptics 30 may be generally J-shaped or C-shaped. The optic 44 has a groove 54 in the side portion of the optic 44 between the anterior surface 46 and posterior surface 48 of the intraocular lens 32. The groove 54 may be formed by two protrusions projecting from the optic 44 of the lens. The groove 54 is located in the peripheral part of the optic 44 so that the function of the optic 44 for projecting images on the retina is not disturbed. Part of the posterior portion 56 of the optic 44 is extending outwardly beyond the anterior portion 58 in the direction of the long axis of the lens. The long axis of an intraocular lens 32 is here implied as the longest axis in which support makes. The extending portion allows the easier insertion of the groove 54 or valley 62 into the opening of the posterior capsule 38.

Figure 2B:
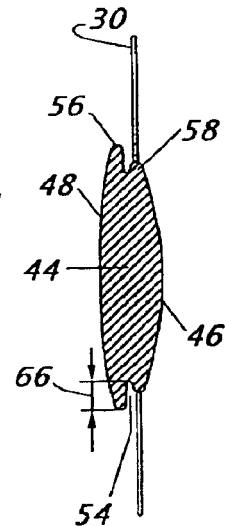
FIG. 2b is a side view of the intraocular lens shown in FIG. 2a of haptics not angulated.
Figure 2C:
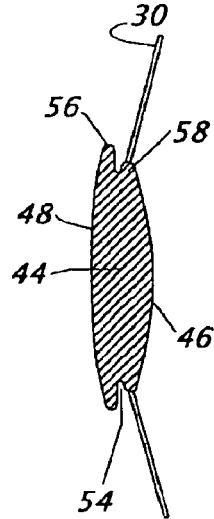
FIG. 2c is a side view of the intraocular lens shown in FIG. 2a with angulated haptics.
Figure 2D:
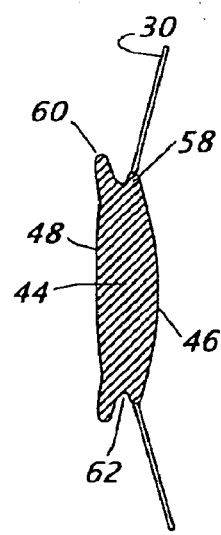
FIG. 2d is a side view of the intraocular lens modified from FIG. 2a having a protrusion extending posterior from the posterior side of the optic.
Figure 2E:
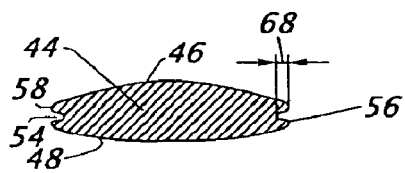
FIG. 2e is a side sectional view of the intraocular lens shown in FIG. 2a having a biconvex optic.
Figure 2F:
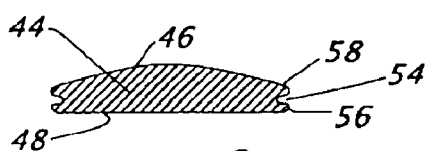
FIG. 2f is a side sectional view of the intraocular lens shown in FIG. 2a having a convex-plano (plano-posterior) optic.

Intraocular lenses provided in accordance with the present invention may have angulated haptics 30 or non-angulated haptics 30 relative to the plane of the optic 44. FIG. 2b depicts a side view of a species of an intraocular lens 32 shown in FIG. 2a. The haptics 30 extend from the optic 44 without angulation from the optic plane. FIG. 2c depicts a side view of a specie of an intraocular lens 32 shown in FIG. 2a. The haptics 30 are extending from the optic 44 in an angulated fashion from the optic plane. FIG. 2d further illustrates a species of an intraocular lens 32 modified from FIG. 2a. In FIG. 2d, the intraocular lens 32 does not have a groove 54 in the side portion of the optic 44, but has a protrusion 60 projecting posteriorly from the optic 44 in an annular fashion. A valley 62 is formed between the optic 44 and the protrusion 60. When the intraocular lens 32 is implanted, the opening of the posterior capsule 38 is engaged with the valley 62 generally over the circumference of the optic 44 so that the opening is closed. FIG. 2e depicts a cross sectional view of the optic 44 illustrating a species of an intraocular lens 32 of FIG. 2a. Both the anterior surface 46 and the posterior surface 48 of the optic 44 are convex. FIG. 2f depicts a cross sectional view of the optic illustrating a specie of an intraocular lens 32 of FIG. 2a. The anterior surface 46 of the optic 44 is convex and the posterior surface 48 of the optic 44 is plano.

Figure 3:
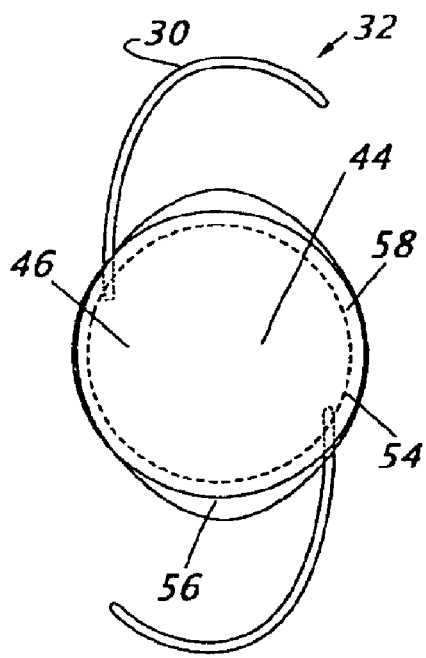
FIG. 3 is a plan view of a second embodied intraocular lens illustrating the haptics attached in clockwise direction.

There are more embodiments for intraocular lenses in accordance with the present invention. The haptics 30 of an intraocular lens 32 in the present invention may extend from the optic 44 outwardly in a clock-wise direction or counter-clock wise direction. FIG. 3 depicts an intraocular lens 32 with haptics 30 extending in clockwise direction. It should be understood that, in the following examples, modifications can be made as illustrated in the FIGS. 2b–2f and FIG. 3.

Figure 4:
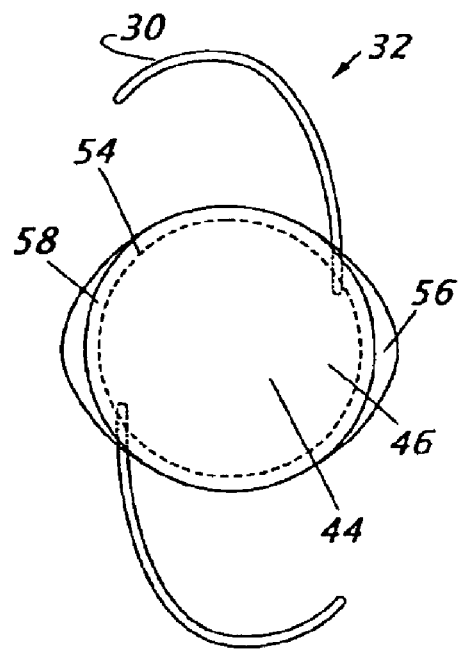
FIG. 4 is a plan view of a third embodied intraocular lens illustrating posterior portions extending in the direction perpendicular to the long axis of the lens.

FIG. 4 depicts a plan view of a further embodiment of the present invention. The intraocular lens 32 has an optic 44 and two haptics 30 to support the optic 44 of the intraocular lens 32. Part of the posterior portion 56 is extending beyond the anterior portion 58 in the direction perpendicular to the long axis of the lens.

Figure 5:
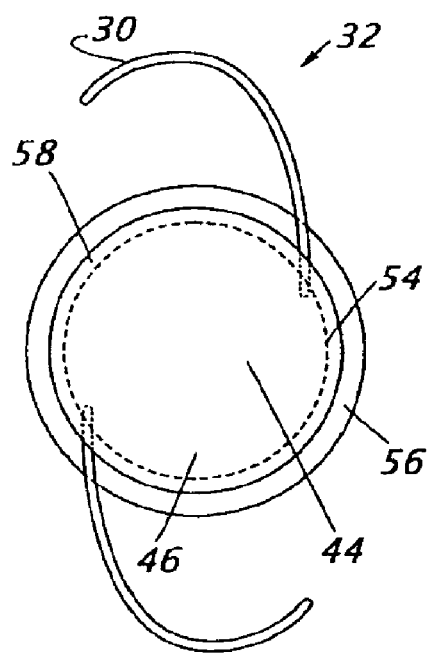
FIG. 5 is a plan view of a fourth embodied intraocular lens illustrating posterior portion extending in a circular fashion.

FIG. 5 depicts a plan view of a further embodiment of the present invention. The intraocular lens 32 has a groove 54 in the side portion between the anterior surface 46 and posterior surface 48. The posterior portion 56 of the optic 44 extends beyond the anterior portion 58 in an annular fashion.

Figure 6:
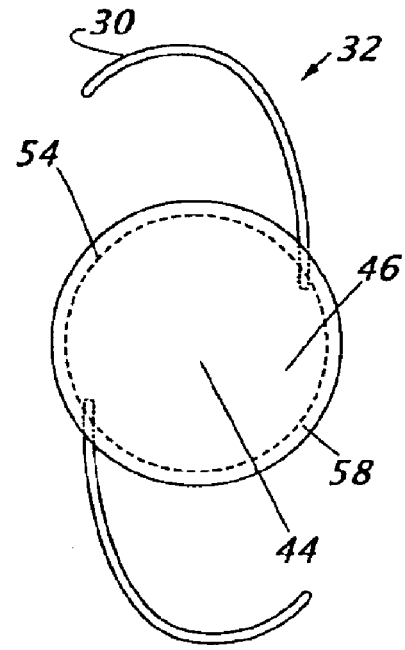
FIG. 6 is a plan view of a fifth embodied intraocular lens.

FIG. 6 depicts a plan view of a further embodiment of the present invention. The intraocular lens 32 has a groove 54 in the side portion between the anterior surface 46 and posterior surface 48.

FIG. 7a depicts a plan view of a further embodiment of the present invention. The intraocular lens 32 in FIG. 7a has haptics 30 made of the same material as the optic 44 of the lens. The haptic 30 and the optic 44 may be made of any material appropriate for clinical use such as polymethylmethacrylate, silicone, hydrogel, acryl and a combination of this group. Part of the posterior portion 56 extends beyond the anterior portion 58 in the direction of the long axis of the lens.

FIG. 7b depicts a side view of the intraocular lens 32 illustrated in FIG. 7a.

FIG. 8 depicts a plan view of a further embodiment of the present invention. The intraocular lens 32 has an optic 44 and two haptics 30 to support the optic 44 of the intraocular lens 32. Part of the posterior portion 56 of the optic 44 is extending beyond the anterior portion 58 in the direction perpendicular to the long axis of the lens.

FIG. 9 depicts a plan view of a further embodiment of the present invention. The intraocular lens 32 has a groove 54 in the side portion between the anterior surface 46 and posterior surface 48. The posterior portion 56 of the optic 44 extends beyond the anterior portion 58 of the lens in an annular fashion.

FIG. 10 depicts a plan view of a further embodiment of the present invention. The intraocular lens 32 has a groove 54 in the side portion between the anterior surface 46 and posterior surface 48.

FIG. 11a depicts a plan view of a further embodiment of the present invention. The intraocular lens 32 has a groove 54 in the side portion between the anterior surface 46 and posterior surface 48. The posterior portion 56 of the optic 44 extends beyond the anterior portion 58 in an annular fashion. The intraocular lens 32 of FIG. 11a may be a one-piece intraocular lens or a lens made from an optic part and a haptic or haptics 30 to be attached. FIG. 11b depicts a side sectional view of an intraocular lens 32 depicted in FIG. 11a of a one-piece lens. The intraocular lens 32 has plate haptics 30 in the plane of the optic 44. FIG. 11c depicts a cross sectional view of the intraocular lens 33 of FIG. 11a of a haptic 30 attached to the optic 44 at the connection 52. FIG. 11d depicts a side view of the optic 44 illustrated in the FIG. 11a. The optic 44 is biconvex.

FIG. 12a depicts a plan view of a further embodiment of the present invention. The intraocular lens 32 has a groove 54 in the side portion between the anterior surface 46 and posterior surface 48. The posterior portion 56 of the optic 44 extends beyond the anterior portion 58 in the direction of the long axis of the intraocular lens 32. A haptic 30 of the intraocular lens 32 of FIG. 12a has a window 64 so that the location of the posterior capsular opening is identified under the operating microscope and placement of the opening of the posterior capsule 38 into a groove 54 is secured. FIG. 12b depicts a cross-sectional view of the intraocular lens 32 of FIG. 12a taken along a line 50—50 of FIG. 12a.

FIG. 13 depicts a plan view of a further embodiment of the present invention. An intraocular lens 32 in the FIG. 13 has an optic 44 and plate haptics 30 of a generally oval configuration. Part of the posterior portion 56 of the optic 44 extends outwardly beyond the anterior portion 58 perpendicular to the long axis of the intraocular lens 32 in a generally oval fashion.

FIG. 14 depicts a plan view of a further embodiment of the present invention. An intraocular lens 32 in the FIG. 14 has an optic 44 and plate haptics 30 of a generally oval configuration.

As will readily be appreciated by those skilled in the art, the foregoing specific embodiments are merely illustrative of the wide variety of intraocular lenses included within the spirit and scope of the present invention.

The optic of intraocular lenses in accordance with the present invention is from 3.0 mm to 8.0 mm. Preferably the diameter of the optic 44 is between 5.0 mm and 6.5 mm. The depth of the groove 68 or that of the valley 62 may be between 0.1 mm and 2.0 mm or longer. The width of the groove 54 or the valley 62 may be between 0.05 mm and 0.5 mm. For easier insertion of the groove 54 of the intraocular lenses 32 or the valley 62 of the intraocular lenses 32 into the opening of the posterior capsule 38, the posterior portion 56 of the optic 44 extends approximately up to 2.0 mm or more beyond the anterior portion 58. The posterior portion 56 of the optic 44 may be partly or entirely (over the entire circumference) extending beyond the anterior portion 58 of the optic 44. Indeed, the posterior portion 56 may be shorter than the anterior portion 58.

In the present invention, in the case in which the optic of an intraocular lens is made of a material on which lens epithelial cells are prone to proliferate or migrate, a large opening may be made in the anterior capsule so that no contact of the optic of the intraocular lens with the rim of the anterior capsular opening occurs and lens epithelial cells do not migrate or proliferate onto the intraocular lens optic. In contrast, in the case in which the optic of an intraocular lens is made of a material on which lens epithelial cells are less likely to proliferate or migrate, a relatively small opening may be made in the anterior capsule and the anterior capsular rim may contact the optic of the intraocular lens but the proliferation or migration of lens epithelial cells onto the optic of the intraocular lens would not occur due to the nature of the optic material. For implantation of an intraocular lens with silicone optic, the opening of the anterior capsule may be small. The optic of an intraocular lens in the present invention is preferably a material that can be folded so that the intraocular lens is inserted into the eye through a small incision in the anterior part of the eye and the astigmatism occurring following cataract surgery is reduced to achieve an earlier recovery of vision.

It should be appreciated that intraocular lenses provided in the present invention have a closing fixture for closing the opening of the posterior capsule. Due to the formation of the groove or the valley in the optic, closing of the opening of the posterior capsule is accomplished easily and effectively. It should also be appreciated that the support extends from the optic so that the stable fixation of the intraocular lenses is secured. Furthermore, due to the relatively simple configuration of intraocular lenses of the present invention, manufacturing of the intraocular lenses is relatively simple and the manufacturing is accomplished without technical difficulty, which minimizes the manufacturing costs.

SURGICAL PROCEDURE OF THE PRESENT INVENTION

The surgical procedure for implantation of intraocular lenses of the present invention is performed as follows: After an incision is made in the anterior part of the eye, i.e., the cornea 18 or the sclera 20, capsulorhexis or capsulotomy of the anterior capsule 36 is performed to make an opening in the anterior capsule 36. The anterior chamber 22 may be filled with a viscoelastic material to maintain the anterior chamber depth before an opening is made in the anterior capsule 36. Then the clouded lens, i.e., the lens cortex and the nucleus, is removed by phacoemulsification or simple delivery of the lens through the incision. Then a viscoelastic material is introduced into the anterior chamber 22 and the lens capsular bag. An opening is preferably made in the center part of the posterior capsule 38 and an intraocular lens 32 is inserted into the posterior capsular opening. Preferably the opening is made in a circular fashion. In order to make a circular opening in the posterior capsule 38 in a well-controlled manner, a viscoelastic material may be introduced into the remaining lens capsular bag following the removal of the clouded lens. Furthermore, a small hole may be made in the center of the posterior capsule 38 by using a fine sharp needle. A small amount of viscoelastic material may be introduced into the Berger's space 40 between the posterior capsule 38 and the vitreous 42 by using a fine cannula through the hole so that the posterior capsule 38 and the anterior surface of the vitreous 42 is separated to avoid the rupturing of the anterior surface of the vitreous 42. An opening may be completed in a circular fashion by using a forceps or a fine bent needle. Accordingly, an opening can be made in the posterior capsule 38 in a well-controlled manner and it is substantially different from the posterior capsule damaged during removal of the clouded lens. This is because the circular opening is resistant to forces and undesired tearing or rupturing can be avoided. The diameter of the opening of the posterior capsule 38 is made smaller than the diameter of the optic 44 of the intraocular lens 32. For example, the diameter of the opening of the posterior capsule 38 may be made 0.5 mm to 3.0 mm smaller than the diameter of the optic 44. Viscoelastic material may be additionally injected to further inflate the lens capsular bag for easier insertion of an intraocular lens 32. The opening of the posterior capsule 38 is made engaged with the groove 54 or the valley 62 of the intraocular lens 32 over the entire circumference so that the opening in the posterior capsule 38 is closed. The optic 44 of the intraocular lens 32 is fixed to the opening of the posterior capsule 38 by simply pressing the optic 44 against the posterior capsule 38 or by a rotation of the optic 44 by using a hook in a "dialing" manner. The viscoelastic material in the anterior chamber 22 and the lens capsular bag is washed away by irrigation with a physiological solution. The incision in the anterior part of the eye is closed.

Accordingly, the present invention provides extremely safe and effective intraocular lenses and the use thereof for reducing complications related to cataract surgery. The use of the intraocular lenses is simple and not difficult for those who are skilled in the current cataract surgical procedure.

While certain preferred embodiments of the present invention have been described and exemplified above, it is not intended to limit the invention to such embodiments, various modifications may be made thereto, without departing from the scope and spirit of the present invention as set forth in the following claims.

What is claimed is:

1. An intraocular lens for implantation into an eye and closing a generally circular opening of a posterior capsule comprising:

an optic;

a haptic, wherein said haptic extends outwardly from the optic, anterior to a groove or a valley, wherein said groove is formed in a side portion of the optic of the intraocular lens, wherein said valley is formed by the optic and a protrusion, wherein said protrusion projects posteriorly from a posterior surface of the optic of the intraocular lens, and whereby said haptic supports the optic; and a closing fixture for closing the opening of the posterior capsule, wherein the closing fixture is the groove or the valley, wherein the groove or the valley is configured to engage with a posterior capsular opening generally over the entire circumference of the groove or the valley such that said posterior capsular opening is closed, wherein said haptic is free of support from a lens capsular opening and is configured to be substantially supported by the equatorial region of the lens capsule.

2. The intraocular lens of claim 1, wherein said optic is made of a material selected from the group consisting of silicone, hydrogel, acrylic polymer and a combination of two or more of this group.

3. The intraocular lens of claim 1, wherein said optic is made of a foldable material.

4. The intraocular lens of claim 1, wherein the diameter of the optic is between about 3.0 mm and about 8.0 mm.

5. The intraocular lens of claim 1, wherein the depth of said groove or said valley is in the range of about 0.1 mm and about 2.0 mm.

6. The intraocular lens of claim 1, wherein the width of said groove or said valley is in the range of about 0.05 mm and about 0.5 mm.

7. A method for closing a generally circular opening of a posterior capsule, comprising:

making an incision in an anterior part of an eye, wherein said anterior part of the eye is a cornea or sclera;

making an opening in an anterior capsule;

making a posterior capsular opening;

inserting the intraocular lens of claim 1 in a lens capsular bag; and engaging the groove or the valley of said intraocular lens with the posterior capsular opening generally over the entire circumference of the groove or the valley, whereby said posterior capsular opening is closed, wherein said haptic is free of support from a lens capsular opening and is configured to be substantially supported by the equatorial region of the lens capsule.

8. An intraocular lens for implantation into an eye and for closing a generally circular opening of a posterior capsule comprising:

an optic, comprising a groove or a valley for closing the opening of the posterior capsule, wherein said groove is formed in a side portion of the optic of the intraocular lens, and wherein said valley is formed by the optic and a protrusion, wherein said protrusion projects posteriorly from a posterior surface of the optic of the intraocular lens, wherein the groove or the valley is engageable with a posterior capsular opening generally over the entire circumference of the groove or the valley such that said posterior capsular opening is closed; and a haptic, wherein said haptic extends outwardly from the optic, anterior to the groove or the valley, whereby said haptic supports the optic, wherein said haptic is free of support from a lens capsular opening and is configured to be substantially supported by the equatorial region of the lens capsule.

9. The intraocular lens of claim 8, wherein said optic is made of a material selected from the group consisting of silicone, hydrogel, acrylic polymer and a combination of two or more of this group.

10. The intraocular lens of claim 8, wherein said optic is made of a foldable material.

11. The intraocular lens of claim 8, wherein the diameter of the optic is between 3.0 mm and 8.0 mm.

12. The intraocular lens of claim 8, wherein a depth of said groove or said valley is in the range of about 0.1 mm and about 2.0 mm.

13. The intraocular lens of claim 8, wherein a width of said groove or said valley is in the range of about 0.05 mm and about 0.5 mm.

14. A method for closing a generally circular opening of a posterior capsule, comprising:

making an incision in an anterior part of an eye, wherein said anterior part of the eye is a cornea or sclera;

making an opening in an anterior capsule;

making a posterior capsular opening;

inserting the intraocular lens of claim 8 in a lens capsular bag; and engaging the groove or the valley of the intraocular lens with the posterior capsular opening generally over the entire circumference of the groove or the valley, whereby said posterior capsular opening is closed, wherein said haptic is free of support from a lens capsular opening and is configured to be substantially supported by the equatorial region of the lens capsule.

* * * * *